United States Patent [19]
Chen et al.

[11] Patent Number: 5,888,968
[45] Date of Patent: Mar. 30, 1999

[54] TFPI FORMULATION

[75] Inventors: Bao-Lu Chen, San Ramon; Rajsharan K. Rana; Maninder S. Hora, both of Danville, all of Calif.

[73] Assignee: Chiron Corporation, Emeryville, Calif.

[21] Appl. No.: 734,997

[22] Filed: Oct. 22, 1996

Related U.S. Application Data

[63] Continuation of Ser. No. 477,677, Jun. 7, 1995, abandoned.

[51] Int. Cl.⁶ .......................... A61K 38/36; C07K 14/745

[52] U.S. Cl. .............................. 514/8; 514/970; 514/973; 514/12; 530/380; 530/395

[58] Field of Search ................................ 514/2, 8, 12, 21, 514/970, 973; 530/380, 381, 395

[56] References Cited

U.S. PATENT DOCUMENTS

| | | | |
|---|---|---|---|
| 5,276,015 | 1/1994 | Khouri et al. | 514/12 |
| 5,358,708 | 10/1994 | Patel et al. | 424/85.1 |
| 5,503,827 | 4/1996 | Woog et al. | 424/85.1 |

FOREIGN PATENT DOCUMENTS

93/25230  12/1993  WIPO.

*Primary Examiner*—John Ulm
*Assistant Examiner*—Christine Saoud
*Attorney, Agent, or Firm*—Banner & Witcoff; Paul B. Witcoff; Robert P. Blackburn

[57] ABSTRACT

Compositions are described that are suitable for formulating TFPI. The compositions allow preparation of pharmaceutically acceptable compositions of TFPI at concentrations above 0.2 mg/mL and above 10 mg/mL.

14 Claims, 10 Drawing Sheets

FIG. I

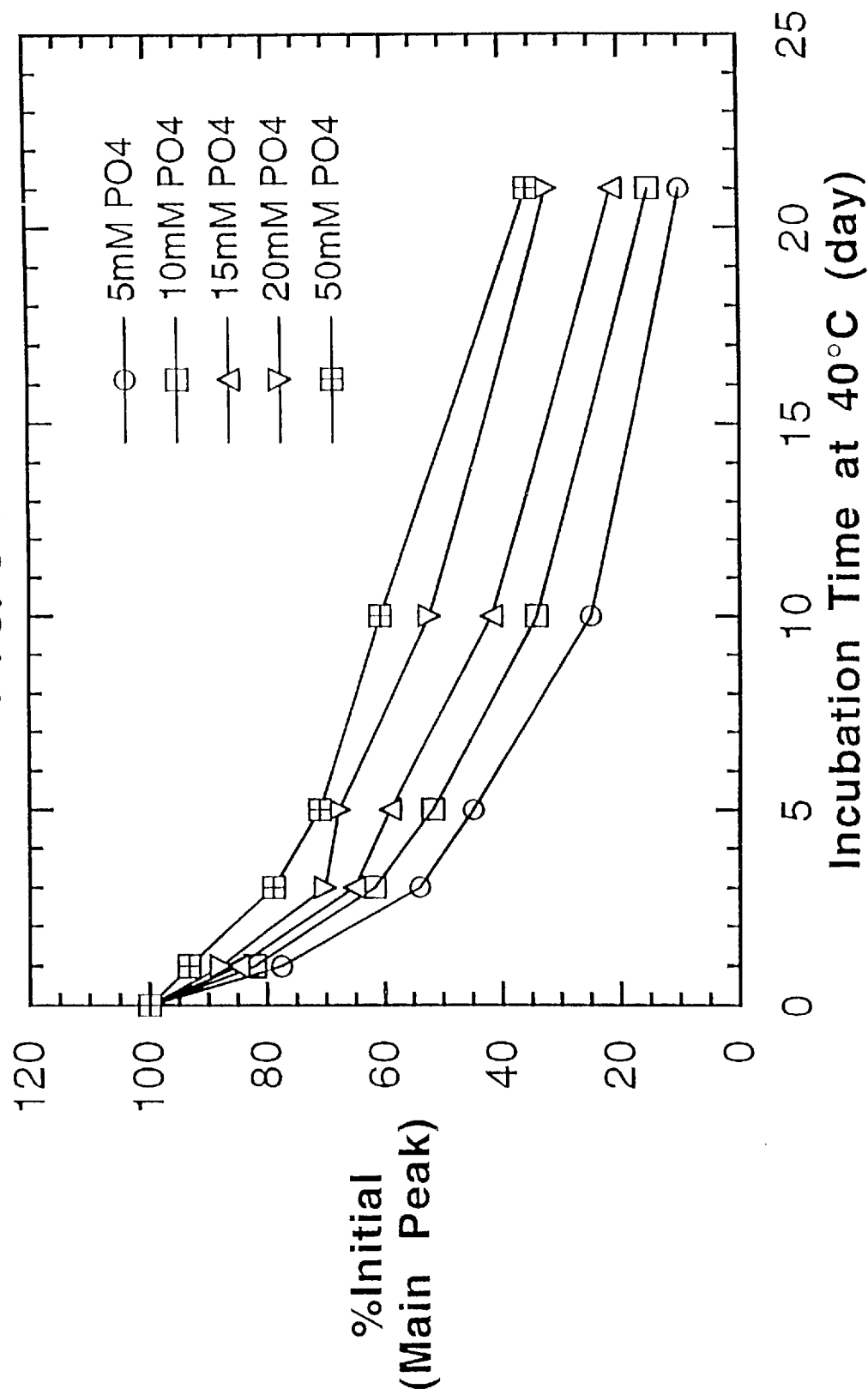

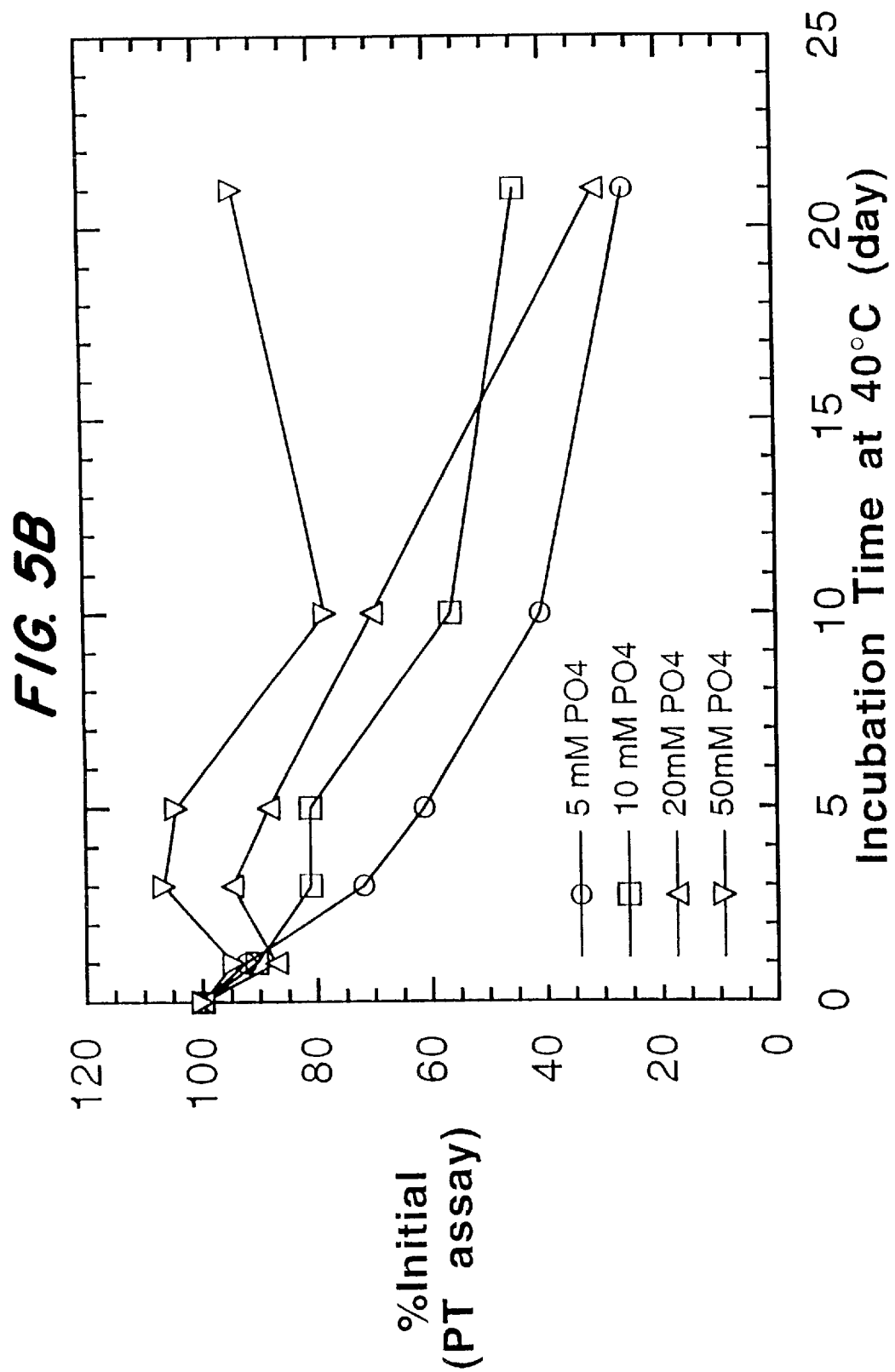

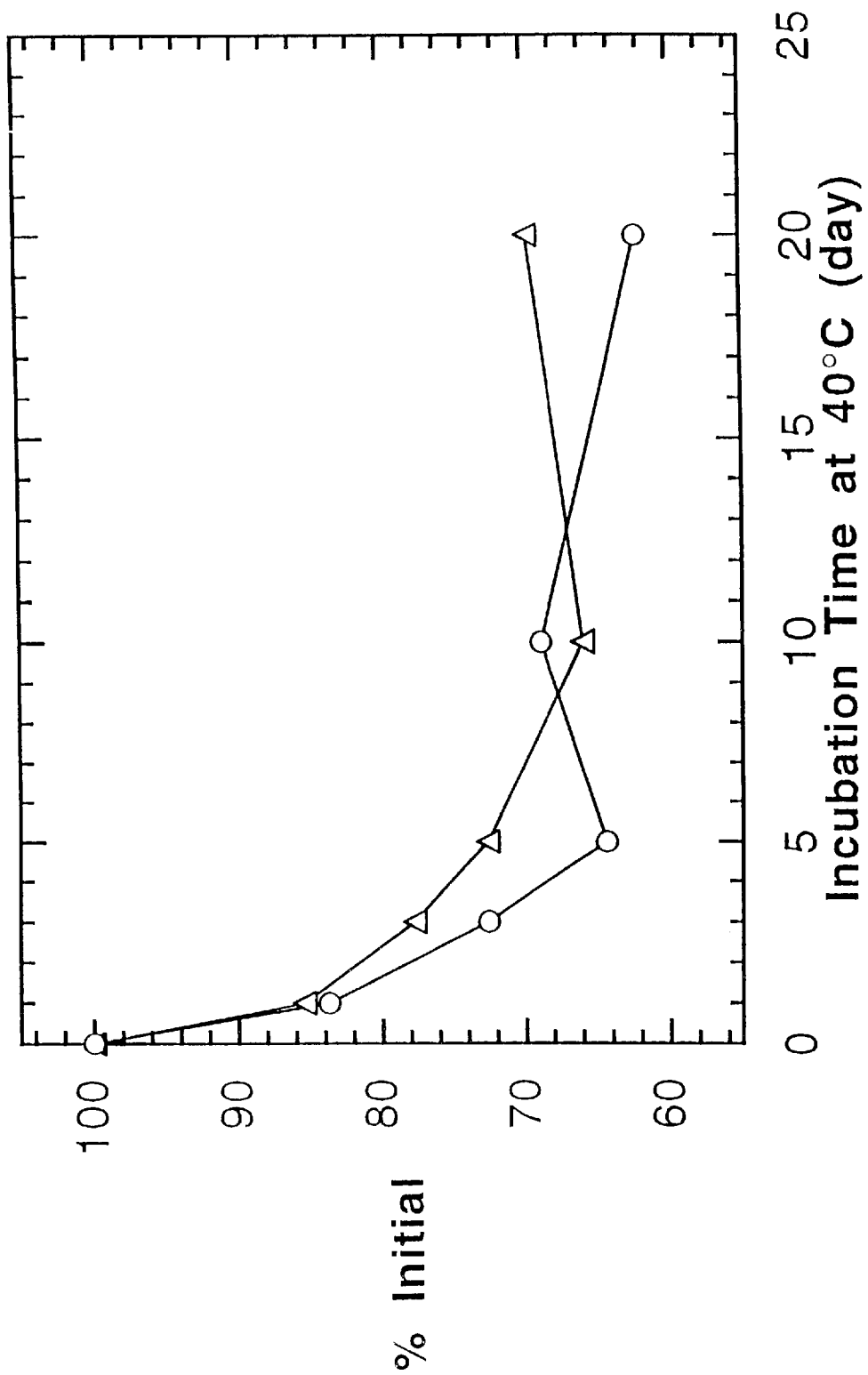

TFPI FORMULATION

This applications is a continuation of application Ser. No. 08/477,677, filed Jun. 7,1995, now abandoned.

TECHNICAL FIELD

The invention relates generally to the field of formulation of proteins useful for attenuating inflammation and coagulation. More specifically, the invention relates to the formulation of Tissue Factor Pathway Inhibitor (TFPI) to achieve concentrations of TFPI useful for administration to patients.

BACKGROUND

TFPI inhibits she coagulation cascade in at least two ways: preventing formation of factor VIIa/tissue factor complex and by binding to the active site of factor Xa. The primary sequence of TFPI, deduced from cDNA sequence, indicates that the protein contains three Kunitz-type enzyme inhibitor domains. The first of these domains is required for the inhibition of the factor VIIa/tissue factor complex. The second Kunitz-type domain is needed for the inhibition of factor Xa. The function of the third Kunitz-type domain is unknown. TFPI has no known enzymatic activity and is thought to inhibit its protease targets in a stoichiometric manner; namely, binding of one TFPI Kunitz-type domain to the active site of one protease molecule. The carboxy-terminal end of TFPI is believed to have a role in cell surface localization via heparin binding and by interaction with phospholipid. TFPI is also known as Lipoprotein Associated Coagulation Inhibitor (LACI), Tissue Factor Inhibitor (TFI), and Extrinsic Pathway Inhibitor (EPI).

Mature TFPI is 276 amino acids in length with a negatively charged amino terminal end and a positively charged carboxy-terminal end. TFPI contains 18 cysteine residues and forms 9 disulphide bridges when correctly folded. The primary sequence also contains three Asn-X-Ser/Thr N-linked glycosylation consensus sites, the asparagine residues located at positions 145, 195 and 256. The carbohydrate component of mature TFPI is approximately 30% of the mass of the protein. However, data from proteolytic mapping and mass spectral data imply that the carbohydrate moieties are heterogeneous. TFPI is also found to be phosphorylated at the serine residue in position 2 of the protein to varying degrees. The phosphorylation does not appear to affect TFPI function.

TFPI has been isolated from human plasma and from human tissue culture cells including HepG2, Chang liver and SK hepatoma cells. Recombinant TFPI has been expressed in mouse C127 cells, baby hamster kidney cells, Chinese hamster ovary cells and human SK hepatoma cells. Recombinant TFPI from the mouse C127 cells has been shown in animal models to inhibit tissue-factor induced coagulation.

A non-glycosylated form of recombinant TFPI has been produced and isolated from *Escherichia coli* (*E. coli*) cells as disclosed in U.S. Pat. No. 5,212,091. This form of TFPI has been shown to be active in the inhibition of bovine factor Xa and in the inhibition of human tissue factor-induced coagulation in plasma. Methods have also been disclosed for purification of TFPI from yeast cell culture medium, such as in Petersen et al, *J.Biol.Chem.* 18:13344–13351 (1993).

Recently, another protein with a high degree of structural identity to TFPI has been identified. Sprecher et al, *Proc. Nat. Acad. Sci., USA* 91:3353–3357 (1994). The predicted secondary structure of this protein, called TFPI-2, is virtually identical to TFPI with 3 Kunitz-type domains, 9 cysteine-cysteine linkages, an acidic amino terminus and a basic carboxy-terminal tail. The three Kunitz-type domains of TFPI-2 exhibit 43%, 35% and 53% primary sequence identity with TFPI Kunitz-type domains 1, 2, and 3, respectively. Recombinant TFPI-2 strongly inhibits the amidolytic activity of factor VIIa/tissue factor. By contrast, TFPI-2 is a weak inhibitor of factor Xa amidolytic activity.

TFPI has been shown to prevent mortality in a lethal *Escherichia coli* (*E. coli*) septic shock baboon model. Creasey et al, *J. Clin. Invest.* 91:2850–2860 (1993). Administration of TFPI at 6 mg/kg body weight shortly after infusion of a lethal dose of *E. coli* resulted in survival in all five TFPI-treated animals with significant improvement in quality of life compared with a mean survival time for the five control animals of 39.9 hours. The administration of TFPI also resulted in significant attenuation of the coagulation response, of various measures of cell injury and significant reduction in pathology normally observed in *E. coli* sepsis target organs, including kidneys, adrenal glands, and lungs.

Due to its clot-inhibiting properties, TFPI may also be used to prevent thrombosis during microvascular surgery. For example, U.S. Pat. No. 5,276,015 discloses the use of TFPI in a method for reducing thrombogenicity of microvascular anastomoses wherein TFPI is administered at the site of the microvascular anastomoses contemporaneously with microvascular reconstruction.

TFPI is a hydrophobic protein and as such, has very limited solubility in aqueous solutions. This limited solubility has made the preparation of pharmaceutically acceptable formulations of TFPI difficult to manufacture, especially for clinical indications which may benefit from administration of high doses of TFPI. Thus, a need exists in the art for pharmaceutically acceptable compositions containing concentrations of TFPI which can be administered to patients in acceptable amounts.

SUMMARY OF THE INVENTION

The invention relates to pharmaceutically acceptable compositions wherein TFPI is present in a concentration of more than 0.2 mg/mL solubilizing agents. The solubilizing agents may be acetate ion, sodium chloride, citrate ion, isocitrate ion, glycine, glutamate, succinate ion, histidine, imidazole and sodium dodecyl sulfate (SDS). In some compositions, TFPI may be present in concentrations of more than 1 mg/mL and more than 10 mg/mL. The composition may also have one or more secondary solubilizers. The secondary solubilizer or solubilizers may be polyethylene glycol (PEG), sucrose, mannitol, or sorbitol. Finally, the composition may also contain sodium phosphate at a concentration greater than 20 mM.

BRIEF DESCRIPTION OF THE DRAWINGS

FIG. 5A shows the percentage of remaining soluble TFPI measured by cation exchange HPLC and FIG. 5B remaining active TFPI by prothrombin time assay as a function of phosphate concentration. The formulation contains 150 µg/mL TFPI prepared in 150 nM NaCl and 0.005% (w/v) POLYSORBATE-80 (sorethytan) at pH 7 with varying concentrations of phosphate.

FIG. 6 shows loss of soluble TFPI at 40° C. measured by both cation-exchange HPLC (triangle) and prothrombin time assay (circle) for 0.5 mg/mL TFPI formulated in 10 mM Na citrate, pH 6 and 150 mM NaCl.

BRIEF DESCRIPTION OF THE INVENTION

Figure 1:
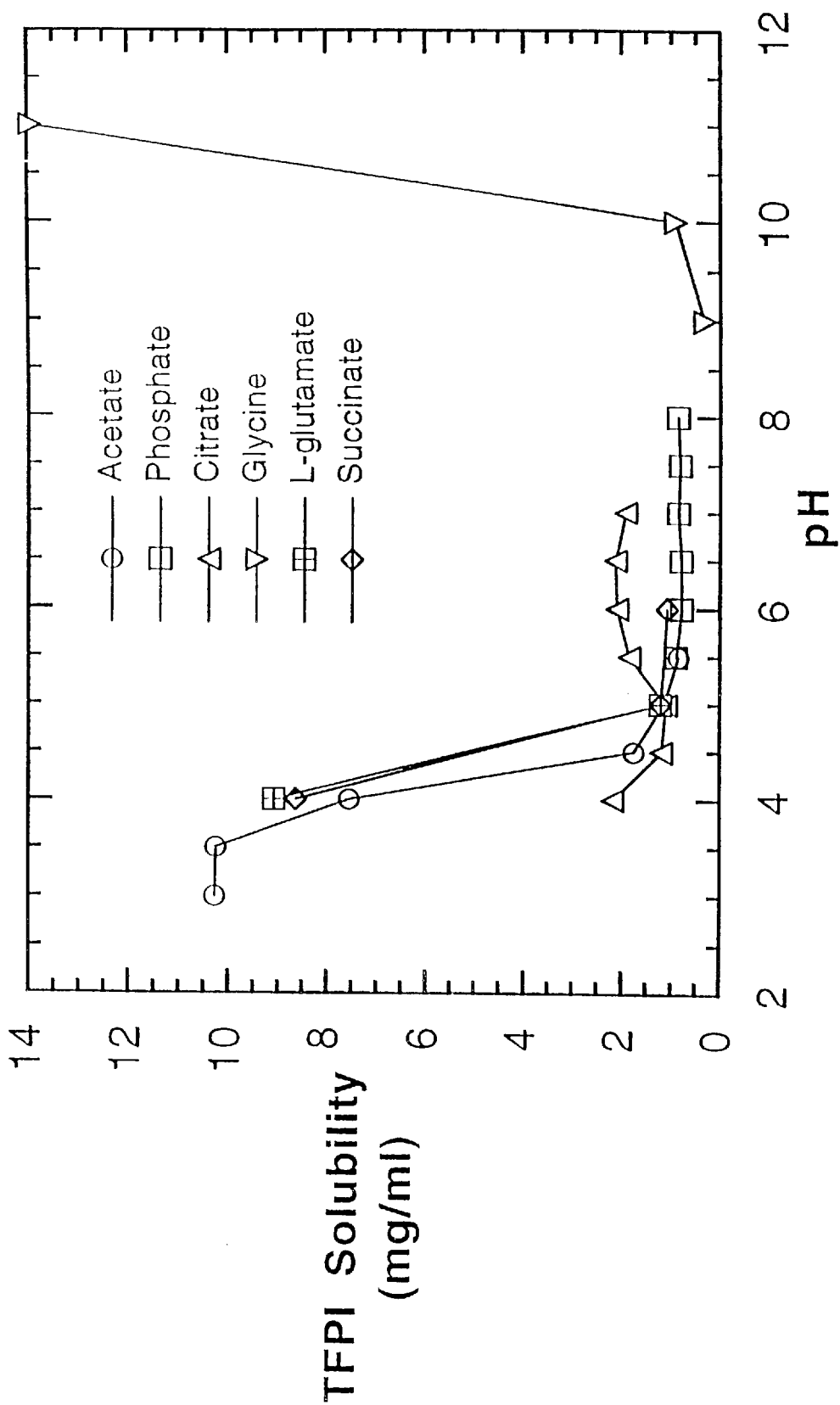
FIG. 1 shows the solubility of TFPI at different pH conditions. About 10 mg/mL TFPI in 2M urea was dialyzed against 20 mM acetate, phosphate, citrate, glycine, L-glutamate and succinate in 150 mM NaCl. The concentration of remaining soluble TFPI after dialysis was measured by UV absorbance after filtering out the precipitates through 0.22 μm filter units.

It has now been found that solubility of TFPI is strongly dependent on pH and, surprisingly, that polyanions such as citrate, isocitrate, and sulfate have profound solubilizing effects on TFPI. This finding is surprising in light of the hydrophobic nature of TFPI and the hydrophilic character of these counterions. Thus, citrate, isocitrate, sulfate as well as other solubilizers described hereinbelow can be used to produce pharmaceutically acceptable compositions having TFPI concentrations sufficient for administration to patients. It has also been shown that other organic molecules can act as secondary solubilizers. These secondary solubilizers include PEG, sucrose, mannitol, and sorbitol.

Further, it has been shown that aggregation of TFPI appears to be the major degradation route at neutral and basic pH conditions and that fragmentation occurs at acidic pH conditions.

DETAILED DESCRIPTION OF THE INVENTION

A. Definitions

As used herein, "TFPI" refers to mature Tissue Factor Pathway Inhibitor. As noted above, TFPI is also known in the art as Lipoprotein Associated Coagulation Inhibitor (LACI), Extrinsic Pathway Inhibitor (EPI) and Tissue Factor Inhibitor (TFI). Muteins of TFPI which retain the biological activity of TFPI are encompassed in this definition. Further, TFPI which has been slightly modified for production in bacterial cells is encompassed in the definition as well. For example, a TFPI analog has an alanine residue at the amino-terminal end of the TFPI polypeptide has been produced in *Escherichia coli*. See U.S. Pat. No. 5,212,091.

As used herein, "pharmaceutically acceptable composition" refers to a composition that does not negate or reduce the biological activity of formulated TFPI, and that does not have any adverse biological effects when formulated TFPI is administered to a patient.

As used herein, "patient" encompasses human and veterinary patients.

As used herein, the term "solubilizer" refers to salts, ions, carbohydrates, amino acids and other organic molecules which, when present in solution, increase the solubility of TFPI above 0.2 mg/mL. Solubilizers may also raise the concentrations of TFPI above 1 mg/mL and above 10 mg/mL. It should be noted that solubilizers may act as stabilizing agents. Stabilizing agents preserve the unit activity of TFPI in storage and may act by preventing formation of aggregates, or by preventing degradation of the TFPI molecule (e.g. by acid catalyzed reactions).

As used herein, the term "secondary solubilizers" refers to organic salts, ions, carbohydrates, amino acids and other organic molecules which, when present in solution with a solubilizer, further increase the solubility of TFPI. Secondary solubilizers may have other effects as well. For example, secondary stabilizers may be useful in adjusting tonicity (e.g. to isotonicity).

B. General Methods

TFPI may be prepared by recombinant methods as disclosed in U.S. Pat. No. 5,212,091, the disclosure of which is herein incorporated by reference. Briefly, TFPI is expressed in *Escherichia coli* cells and the inclusion bodies containing TFPI are isolated from the rest of the cellular material. The inclusion bodies are subjected to sulfitolysis, purified using ion exchange chromatography, refolded by disulfide interchange reaction and the refolded, active TLPI purified by cation exchange chromatography. TFPI may also be produced in yeast as disclosed in co-pending U.S. Ser. No. 08/286,530.

TFPI activity may be tested by the prothrombin time assay (PTT assays). Bioactivity of TFPI was measured by the prothrombin clotting time using a model RA4 Coag-A-Mate from Organon Teknika Corporation (Oklahoma City, Okla.). TFPI samples were first diluted to 9 to 24 ug/mL with a TBSA buffer (50 mM Tris, 100 mM NaCl, 1 mg/mL BSA, pH 7.5). Then 10 uL of Varify 1 (pooled normal plasma from Organon Teknika Corp.) was mixed with 90 uL of diluted TFPI samples in a sample tray and warmed to 37° C. in the instrument. Finally Simplastin Excel (Thromboplastin from Organon Teknika Corp.) was added to start the clotting. The time delay in clotting due to anticoagulant activity of TFPI was measured and converted into TFPI concentration in the measured samples by comparison to a TFPI standard curve.

The amount of soluble TFPI may also be quantified by measuring the area of the main peak on a cation exchange chromatogram. HPLC analysis of TFPI samples was performed using a Waters 626 LC system (Waters Corporation, Milford, Mass.) equipped with a Water 717 plus heater/cooler autosampler. Data acquisition was processed by a Turbochrom system from Perkin-Elmer.

The cation exchange (IEX) method used a Pharmacia Mono S HR 5/5 glass column. The column was equilibrated in 80% buffer A (20 mM sodium acetate trihydrate:acetonitrile solution (70:30 v/v) at pH 5.4) and 20% buffer B (20 mM sodium acetate trihydrate-1.0 M ammonium chloride-:acetonitrile solution (70:30 v/v) at pH 5.4). After a sample was injected, a gradient was applied to elute the TFPI at a flow rate of 0.7 mL/min from 20% buffer B to 85% buffer B in 21 minutes. Eluting TFPI species were detected by absorbance at 214 nm. The main peak (monomer TFPI) was found to elute at about 18 minutes. Loss of soluble TFPI was quantified by integrating remaining peak area of the main peak.

Al reagents are U.S.P. or A.C.S. grade. Suppliers include J. T. Baker and Sigma Co. (St. Louis, Mo.).

C. EXAMPLES

Example 1

About 10 mg/mL TFPI in 2M urea was dialyzed against one of the following: 20 mM acetate, 20 mM phosphate, 20 mM citrate, 20 mM glycine, 20 mM L-glutamate or 20 mM succinate in 150 mM NaCl as described above. 6–10 mg/mL TFPI bulk stock was loaded into Spec/Por 7 dialysis tubings (MW cutoff 3,500). Dialysis was carried out either at 4° C. or ambient temperature. Three changes of buffer at a protein solution to buffer ratio: 1 to 50–100, were made during course of dialysis over 12 to 24 hr time period. After dialysis, TFPI solution was filtered by Costar 0.22 micron filter units to separate precipitated TFPI from soluble TFPI. The solubility of TFPI was then measured by UV/Vis absorbance assuming an absorptivity 0.68 $(mg/mL)^{-1} cm^{-1}$ at 278 nm. The solutions were prepared at various pH levels by titration with HCl or NaOH.

Figure 2:
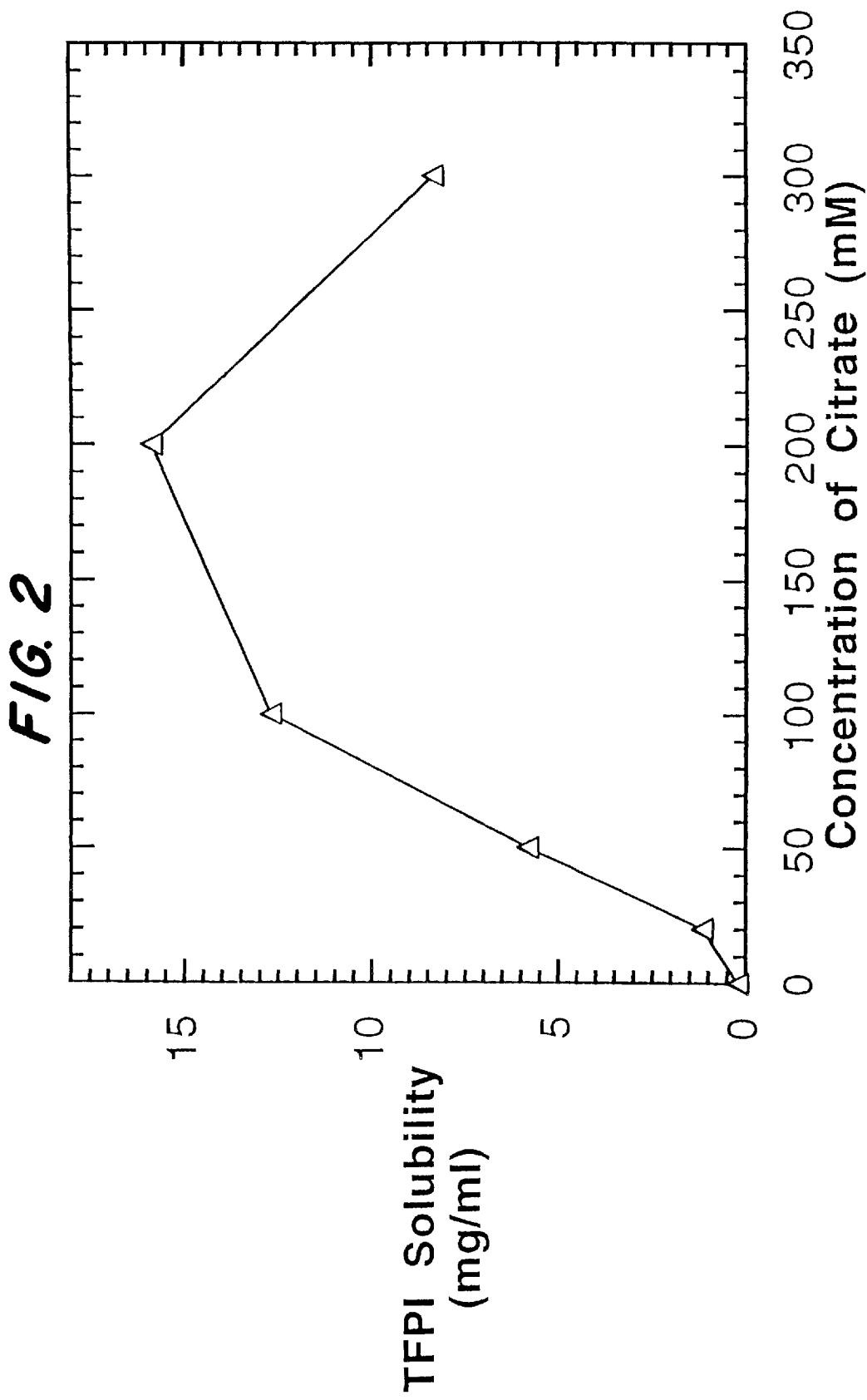
FIG. 2 shows the solubility of TFPI as a function of concentration of citrate in the presence of 10 mM Na phosphate at pH 7. TFPI solubility increases with increasing concentration of citrate.
Figure 3:
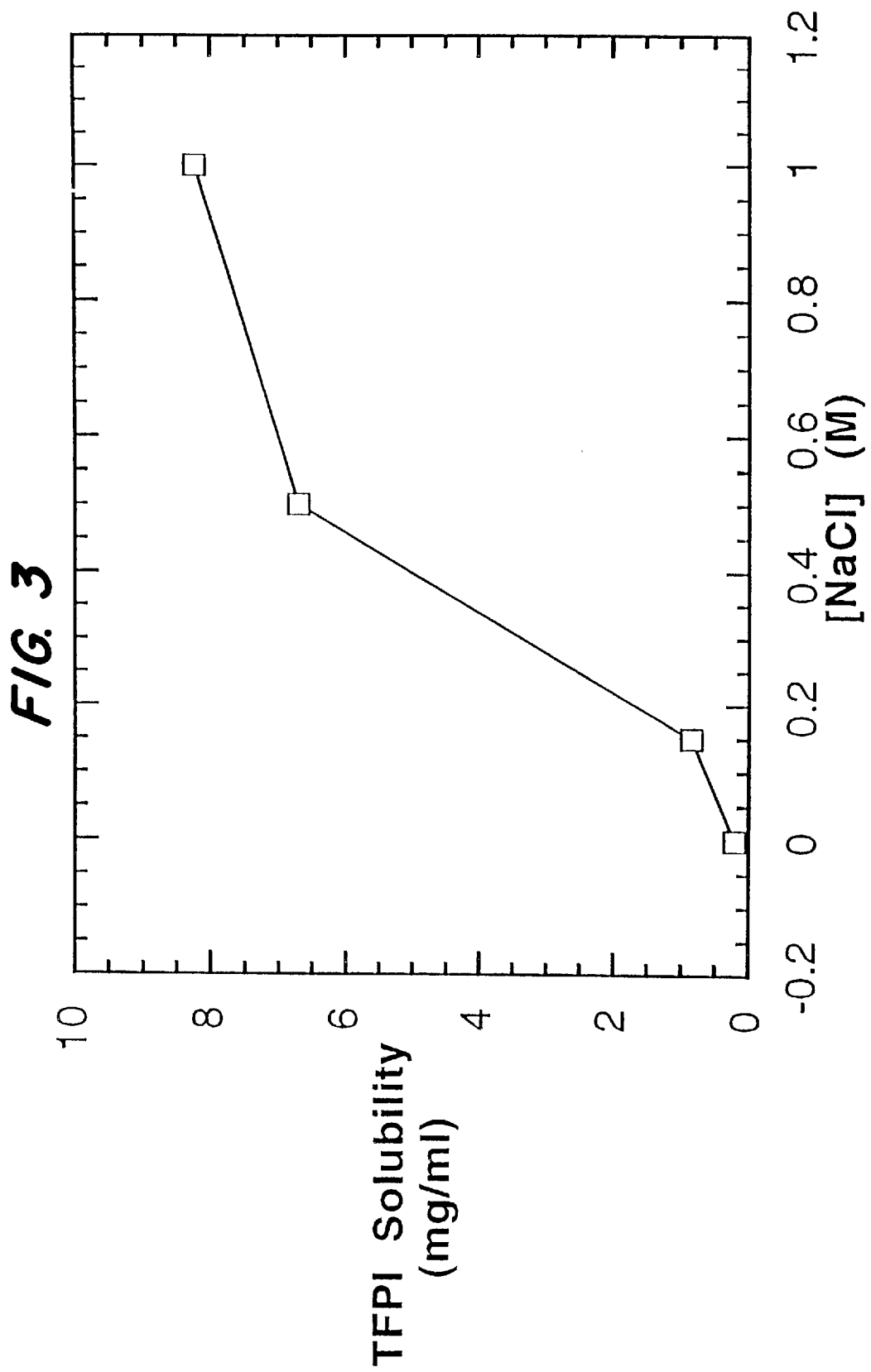
FIG. 3 shows the solubility of TFPI as a function of concentration of NaCl. TFPI solubility increases with increasing salt concentration, indicating salt promotes solubility of TFPI.

After completion of dialysis, the precipitates were filtered through 0.22 μm filter units. The concentration of remaining soluble TFPI after dialysis was measured by UV absorbance. FIG. 1 shows the results of these experiments. Solubility of TFPI increased greatly in solutions containing 20 mM acetate, 20 mM phosphate, 20 mM L-glutamate and 20 mM succinate at pH levels below 7 and particularly at or below pH 4.5. Solubility of TFPI was also substantially increased in solutions containing 20 mM glycine above pH 10. FIG. 2 shows the solubility of TFPI as a function of concentration of citrate ion in the presence of 10 mM Na phosphate at pH 7. TFPI solubility increases with increasing concentration of citrate. FIG. 3 shows the solubility of TFPI as a function of concentration of NaCl at pH 7.0. TFPI solubility increases with increasing salt concentration, indicating salt promotes solubility of TFPI.

The solubility of TFPI was studied using a number of different solubilizers and secondary solubilizers. Table 1 shows solubility of TFPI in varying buffer solutions measured by UV absorbance after dialyzing 6 to 10 mg/mL TFPI into these buffer solutions.

TABLE 1

| Content | pH | Solubility c (mg/ml) uv |
|---|---|---|
| Salt Effect | | |
| 10 mM Na$_3$PO$_4$ | 7 | 0.21 |
| 10 mM Na$_3$PO$_4$, 150 mM NaCl | 7 | 0.72 |
| 20 mM Na$_3$PO$_4$, 150 mM NaCl | 7 | 0.85 |
| 20 mM Na$_3$PO$_4$, 0.5 M NaCl | 7 | 6.71 |
| 20 mM Na$_3$PO$_4$, 1 M NaCl | 7 | 8.24 |
| pH effect | | |
| 20 mM NaOAc, 150 mM NaCl | 3 | 10.27 |
| 20 mM NaOAc, 150 mM NaCl | 3.5 | 10.25 |
| 20 mM NaOAc, 150 mM NaCl | 4 | 7.54 |
| 20 mM NaOAc, 1S0 mM NaCl | 4.5 | 1.75 |
| 20 mM NaOAc, 150 mM NaCl | 5 | 1.15 |
| 20 mM NaOAc, 150 mM NaCl | 5.5 | 0.85 |
| 20 mM Na$_3$PO$_4$, 150 mM NaCl | 5.5 | 0.89 |
| 20 mM Na$_3$PO$_4$, 150 mM NaCl | 6 | 0.78 |
| 20 mM Na$_3$PO$_4$, 150 mM NaCl | 6.5 | 0.79 |
| 20 mM Na$_3$PO$_4$, 150 mM NaCl | 7 | 0.85 |
| 20 mM Na$_3$PO$_4$, 150 mM NaCl | 7.5 | 0.82 |
| 20 mM Na$_3$PO$_4$, 150 mM NaCl | 8 | 0.86 |
| 20 mM NaCitrate, 150 mM NaCl | 4 | 2.17 |
| 20 mM NaCitrate, 150 mM NaCl | 4.5 | 1.19 |
| 20 mM NaCitrate, 150 mM NaCl | 5 | 1.1 |
| 20 mM NaCitrate, 150 mM NaCl | 5.5 | 1.84 |
| 20 mM NaCitrate, 150 mM NaCl | 6 | 2.09 |
| 20 mM NaCitrate, 150 mM NaCl | 6.5 | 2.12 |
| 20 mM NaCitrate, 150 mM NaCl | 7 | 1.92 |
| 20 mM Glycine, 150 mM NaCl | 9 | 0.32 |
| 20 mM Glycine, 150 mM NaCl | 10 | 0.9 |
| 20 mM Glycine, 150 mM NaCl | 11 | 13.94 |
| 20 mM L-Glutamate, 150 mM NaCl | 4 | 9.07 |
| 20 mM L-Glutamate, 150 mM NaCl | 5 | 1.21 |
| 20 mM Succinate, 150 mM NaCl | 4 | 8.62 |
| 20 mM Succinate, 150 mM NaCl | 5 | 1.21 |
| 20 mM Succinate, 150 mM NaCl | 6 | 1.07 |
| Citrate | | |
| 10 mM Na$_3$PO$_4$, 20 mM NaCitrate | 7 | 1.16 |
| 10 mM Na$_3$PO$_4$, 50 mM NaCiirate | 7 | 5.81 |
| 10 mM Na$_3$PO$_4$, 100 mM NaCitrate | 7 | 12.7 |
| 10 mM Na$_3$PO$_4$, 200 mM NaCitrate | 7 | 15.9 |
| 10 mM Na$_3$PO$_4$, 300 mM NaCitrate | 7 | 8.36 |
| Mg2+, Ca2+ and polyphosphate | | |
| 10 mM Na$_3$PO$_4$, 150 mM NaCl, 1 mM MgCl2 | 7 | 0.66 |
| 10 mM Na$_3$PO$_4$, 150 mM NaCl, 10 mM MgCl2 | 7 | 1.02 |
| 10 mM Na$_3$PO$_4$, 150 mM NaCl, 0.1 mM CaCl2 | 7 | 0.67 |
| 10 mM Na$_3$PO$_4$, 150 mM NaCl, 1 mM CaCl2 | 7 | 0.71 |
| 10 mM Na$_3$PO$_4$, 150 mM NaCl, 10 mM triphosphate | 7 | 3.64 |
| 10 mM Na$_3$PO$_4$, 5% PEG-400 | 7 | 0.07 |
| 10 mM Na$_3$PO$_4$, 10 mM EDTA | 7 | 0.36 |
| 10 mM Na$_3$PO$_4$, 100 mM Na2SO4 | 7 | 5.08 |
| 10 mM Na$_3$PO$_4$, 100 mM L-aspartic acid | 7 | 0.4 |
| 10 mM Na$_3$PO$_4$, 100 mM Succinic acid | 7 | 2.33 |
| 10 mM Na$_3$PO$_4$, 100 mM Tartaric acid | 7 | 2.56 |
| 20 mM Na$_3$PO$_4$, 100 mM Maleic acid | 7 | 0.11 |
| 20 mM Na$_3$PO$_4$, 100 mM Malic acid | 7 | 1.87 |
| 10 mM Na$_3$PO$_4$, 100 mM L-glutamic acid | 7 | 0 |
| 10 mM Na$_3$PO$_4$, 150 mM NaCl | 7 | 0.25 |
| 10 mM Na$_3$PO$_4$, 100 mM isocitrate | 7 | 10.83 |
| NaOAc, NaPO4 and NaCl | | |
| 10 mM NaOAc, 150 mM NaCl | 4.5 | 1.76 |
| 10 mM NaOAc | 4.5 | 4.89 |
| 10 mM NaOAc | 5.5 | 4.95 |
| 10 mM NaOAc | 6.5 | 5.1 |
| 10 mM NaOAc | 7 | 5.87 |
| 10 mM Na$_3$PO$_4$, 150 mM NaCl | 4.5 | 0.14 |
| 10 mM Na$_3$PO$_4$ | 4.5 | 4.97 |
| 10 mM Na$_3$PO$_4$ | 5.5 | 0.79 |
| 10 mM Na$_3$PO$_4$ | 6.5 | 0.091 |
| 10 mM Na$_3$PO$_4$ | 7 | 0.94 |
| 50 mM NaOAc | 5 | 5.24 |
| 5 mM NaOAc | 5.5 | 4.59 |
| 10 mM NaOAc | 5.5 | 5.05 |
| 20 mM NaOAc | 5.5 | 5.04 |
| 50 mM NaOAc | 5.5 | 5.71 |
| 100 mM NaOAc | 5.5 | 1.4 |
| 200 mM NaOAc | 5.5 | 1.32 |
| 5 mM NaOAc, 5 mM NaCl | 5.5 | 4.85 |
| 5 mM NaOAc, 10 mM NaCl | 5.5 | 5.04 |
| 5 mM NaOAc, 50 mM NaCl | 5.5 | 0.56 |
| 5 mM NaOAc, 100 mM NaCl | 5.5 | 0.43 |
| 5 mM NaOAc, 200 mM NaCl | 5.5 | 0.8 |
| 5 mM NaOAc | 4.5 | 7.27 |
| 10 mM NaOAc | 4.5 | 6.5 |
| 20 mM NaOAc | 4.5 | 8.32 |
| 50 mM NaOAc | 4.5 | 9.17 |
| 5 mM NaOAc | 5.5 | 8.98 |
| 10 mM NaOAc | 5.5 | 8.08 |
| 20 mM NaOAc | 5.5 | 8.99 |
| 50 mM NaOAc | 5.5 | 2.92 |
| 5 mM NaOAc, 150 mM NaCl | 4.5 | 2.6 |
| 10 mM NaOAc, 150 mM NaCl | 4.5 | 2.59 |
| 20 mM NaOAc, 150 mM NaCl | 4.5 | 2.55 |
| 50 mM NaOAc, 150 mM NaCl | 4.5 | 2.1 |
| 5 mM NaOAc, 150 mM NaCl | 5.5 | 0.65 |

TABLE 1-continued

| Content | pH | Solubility c (mg/ml) uv |
|---|---|---|
| 10 mM NaOAc, 150 mM NaCl | 5.5 | 0.69 |
| 20 mM NaOAc, 150 mM NaCl | 5.5 | 0.74 |
| 50 mM NaOAc, 150 mM NaCl | 5.5 | 0.91 |
| Hydrophobic chain length | | |
| 10 mM Na$_3$PO$_4$, 50 mM Formic acid | 4 | 0.12 |
| 10 mM Na$_3$PO$_4$, 50 mM Acetic acid | 7 | 0.16 |
| 10 mM Na$_3$PO$_4$, 50 mM Propanoic acid | 7 | 0.16 |
| 10 mM Na$_3$PO$_4$, 50 mM Butanoic acid | 7 | 0.13 |
| 10 mM Na$_3$PO$_4$, 50 mM Pentanoic acid | 7 | 0.14 |
| 10 mM Na$_3$PO$_4$, 50 mM Hexanoic acid | 7 | 0.11 |
| Others | | |
| 20 mM NaOAc, 3% Mannitol, 2% Sucrose, 5% PEG-400 | 4 | 19.9 |
| 20 mM Na Citrate, 3% Mannitol, 2% Sucrose, 5% PEG-400 | 6.5 | 0.72 |
| 20 mM Na Citrate, 150 mM NaCl, 5% PEG-400 | 6.5 | 2.18 |
| 20 mM NaOAc, 150 mM NaCl, 5% PEG-400 | 4 | 19.8 |
| 20 mM Na Citrate, 130 mM NaCl, 1% Glycine, 0.25% 5% PEG-400 | 6.5 | 1.48 |
| 20 mM Na Citrate, 130 mM NaCl, 1% Glycine, 0.25% "TWEEN-80 (surface active agent)" | 6.5 | 1.32 |
| 5 mM NaAcetate | 5.5 | 8.9 |
| 5 mM NaAcetate, 8% Sucrose | 5.5 | 11 |
| 5 mM NaAcetate, 0.01% | 5.5 | 7 |
| 5 mM NaAcetate, 8% Sucrose, 0.01% Polysorbate-80 | 5.5 | 12 |
| 10 mM NaAcetate | 5.5 | 7.6 |
| 10 mM NaAcetate, 8% Sucrose | 5.5 | 10 |
| 10 mM NaAcetate, 8% Sucrose, 0.01% Polysorbate-80 | 5.5 | 12.1 |
| 5 mM NaAcetate, 5% Sorbitol | 5.5 | 7.8 |
| 5 mM NaAcetate, 4.5% Mannitol | 5.5 | 9.2 |
| 5 mM Histidine | 6 | 5.5 |
| 5 mM Histidine | 6.5 | 1 |
| 5 mM NaCitrate | 5.5 | 0.1 |
| 5 mM NaCitrate | 6 | 0.1 |
| 5 mM NaCitrate | 6.5 | 0.1 |
| 5 mM NaSuccinate | 5.5 | 0.6 |
| 5 mM NaSuccinate | 6 | 0.3 |
| 5 mM NaSuccinate | 6.5 | 0.2 |
| 10 mM Imidazole | 6.5 | 2.5,10.8 |
| 10 mM Imidazole | 7 | 0.8 |
| 10 mM Imidazole, 8% Sucrose | 6.5 | 12.2 |
| 5 mM NaAcetate | 6 | 8.2 |
| 10 mM Imidazole, 5 mM NaAcetate | 6.5 | 12.8 |
| 10 mM NaCitrate | 6 | 0.2 |
| 100 mM NaCitrate | 6 | 8.1 |
| 100 mM NaCitrate | 7 | 9.3 |
| 10 mM Naphosphate, 260 mM Na2SO4 | 6 | 9.1 |
| 10 mM NaPhosphate, 100 mM NaCitrate | 8 | 8.8 |
| 10 mM NaCitrate, 1% L-glutamic acid | 6 | 4.6 |
| 10 mM NaCitrate, 2% L-lysine | 6 | 1.1 |
| 10 mM NaCitrate, 0.5% L-aspartic acid | 6 | 0.4 |
| 10 mM NaCitrate, 0.1% Phosphate glass | 7 | 5.9 |
| 10 mM Tris, 100 mM NaCitrate | 8 | 8.5 |
| 10 mM NaCitrate, 1 M Glycine | 6 | 0.3 |
| 10 mM NaCitrate, 300 mM Glycine | 6 | 0.3 |
| 10 mM NaCitrate, 280 mM Glycerol | 6 | 0.3 |
| 10 mM NaCitrate, 0.5 M (NH4)2SO4 | 6 | 8.3 |
| 10 mM NaCitrate, 120 mM (NH4)2SO4 | 6 | 8.8 |
| 10 mM NaCitrate, 260 mM Na2SO4 | 6 | 9.4 |
| 10 mM Na$_3$PO$_4$, 0.1% Phosphate glass | 7 | 15.8 |
| 10 mM NaCitrate, 0.1% SDS | 6 | 11.2 |
| 10 mM NaCitrate, 0.02% SDS | 6 | 7.8 |
| 10 mM NaAcetate, 8% PEG-400 | 5.5 | 13.7 |
| 10 mM NaAcetate, 150 mM NaCl, 8% PEG-400 | 5.5 | 0.6 |
| 10 mM NaAcetate, 8% PEG-400 | 6 | 16.2 |
| 10 mM NaCitrate, 8% PEG-400 | 6 | 0.2 |

Example 2

Figure 4:
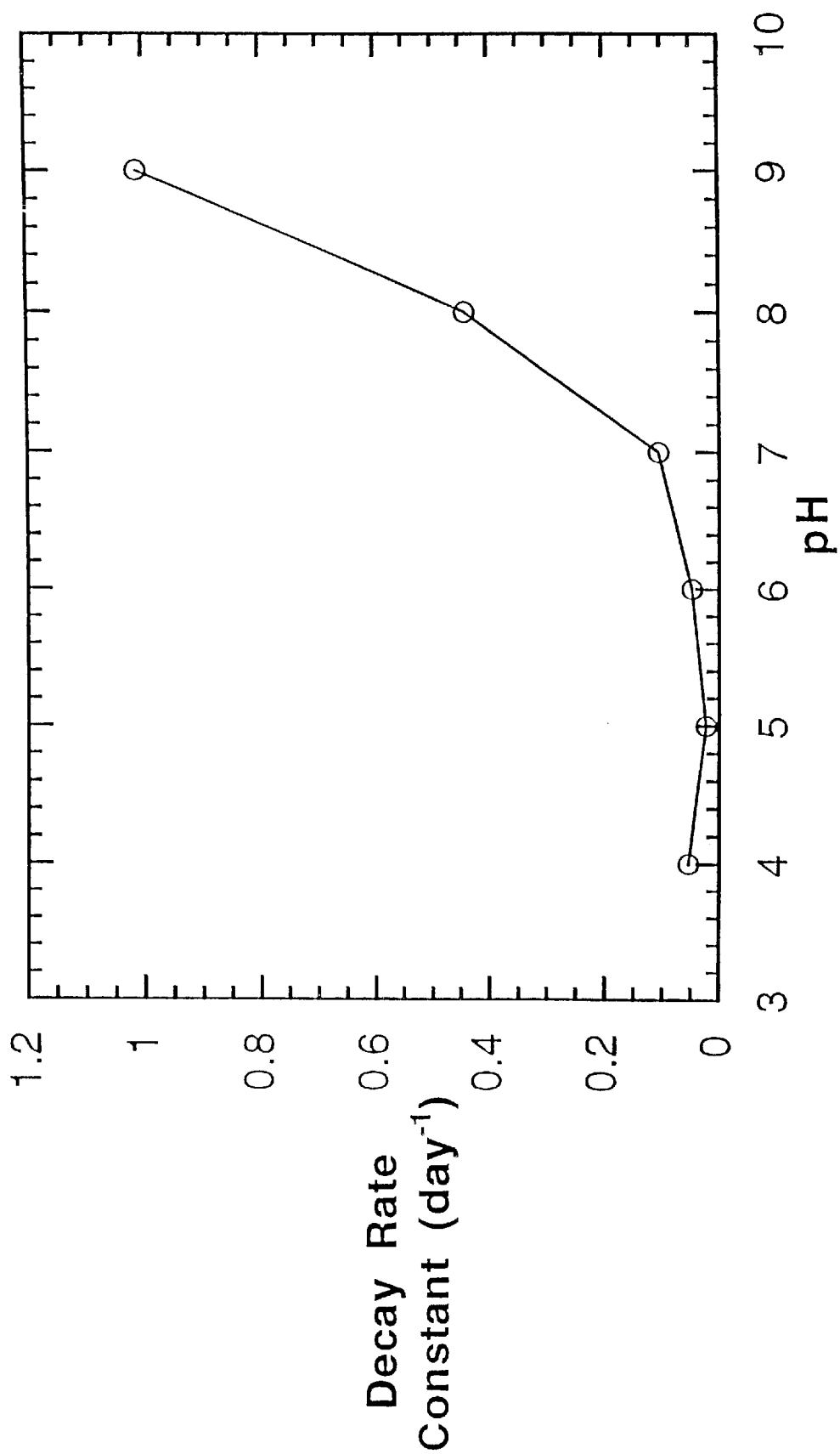
FIG. 4 shows effect of pH on the stability of TFPI prepared in 10 mM Na phosphate, 150 mM NaCl and 0.005% (w/v) polysorbate-80. Stability samples containing 150 µg/mL TFPI were incubated at 40° C. for 20 days. Kinetic rate constant for the remaining soluble TFPI was analyzed by following decrease of the main peak on cation exchange chromatograms.

The stability of TFPI stored at various pH conditions was tested. TFPI was prepared by dialysis as above in 10 mM Na phosphate, 150 mM NaCl and 0.005% (w/v) POLYSORBATE-80. Stability samples containing 150 μg/mL TFPI were incubated at 40° C. for 20 days. Kinetic rate constant for the remaining soluble TFPI was analyzed by following decrease of the main peak on cation exchange chromatograms. As can be seen in FIG. 4, the decay rate constant increases at pH above 6.0, indicates more aggregation at higher pH conditions.

TFPI was also formulated at a concentration of 150 μg/mL in 150 mM NaCl and 0.005% (w/v) POLYSORBATE-80 at pH 7 with varying concentrations of phosphate. FIG. 5A shows the percentage of remaining soluble TFPI measured by the cation exchange HPLC. Increasing concentrations of phosphate ion in solution resulted in higher levels of soluble TFPI remaining after incubation at 40° C. Higher levels of phosphate ion also resulted in higher levels of active TFPI as assayed by the prothrombin time assay. These results are shown in FIG. 5B.

Stability of TFPI at a concentration of 0.5 mg/mL and formulated in 10 mM Na citrate, pH 6 and 150 mM NaCl was also tested at 40° C. over a 40 day period. As seen in FIG. 6, cation-exchange HPLC (triangle) shows the presence of soluble TFPI at levels greater than 60% initial, even after the 40 day incubation. In like manner, the prothrombin time assay (circle) shows the presence of active TFPI at levels greater than 60% initial, even after the 40 day incubation.

Figure 7:
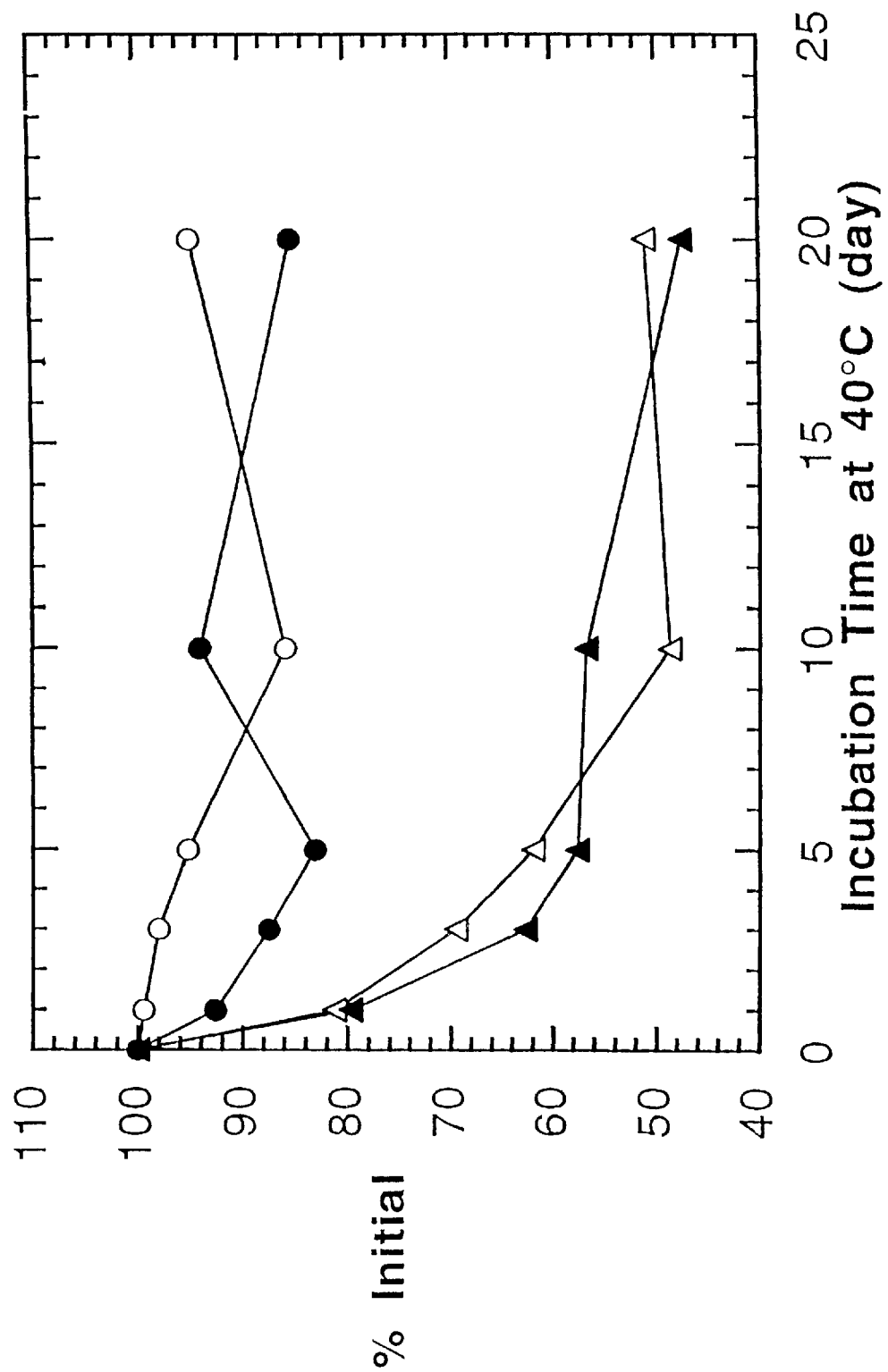
FIG. 7 shows loss of soluble TFPI at 40° C. measured by both cation-exchange HPLC (open symbol) and prothrombin time assay (closed symbol) for 0.5 mg/mL TFPI formulated in 10 mM Na phosphate, pH 6 and either 150 mM NaCl (triangle) or 500 mM NaCl (circle).

FIG. 7 shows loss of soluble TFPI at 40° C. measured by both cation-exchange HPLC (open symbol) and prothrombin time assay (closed symbol) for 0.5 mg/mL TFPI formulated in 10 mM Na phosphate, pH 6 and either 150 mM NaCl (triangle) or 500 mM NaCl (circle).

Figure 8:
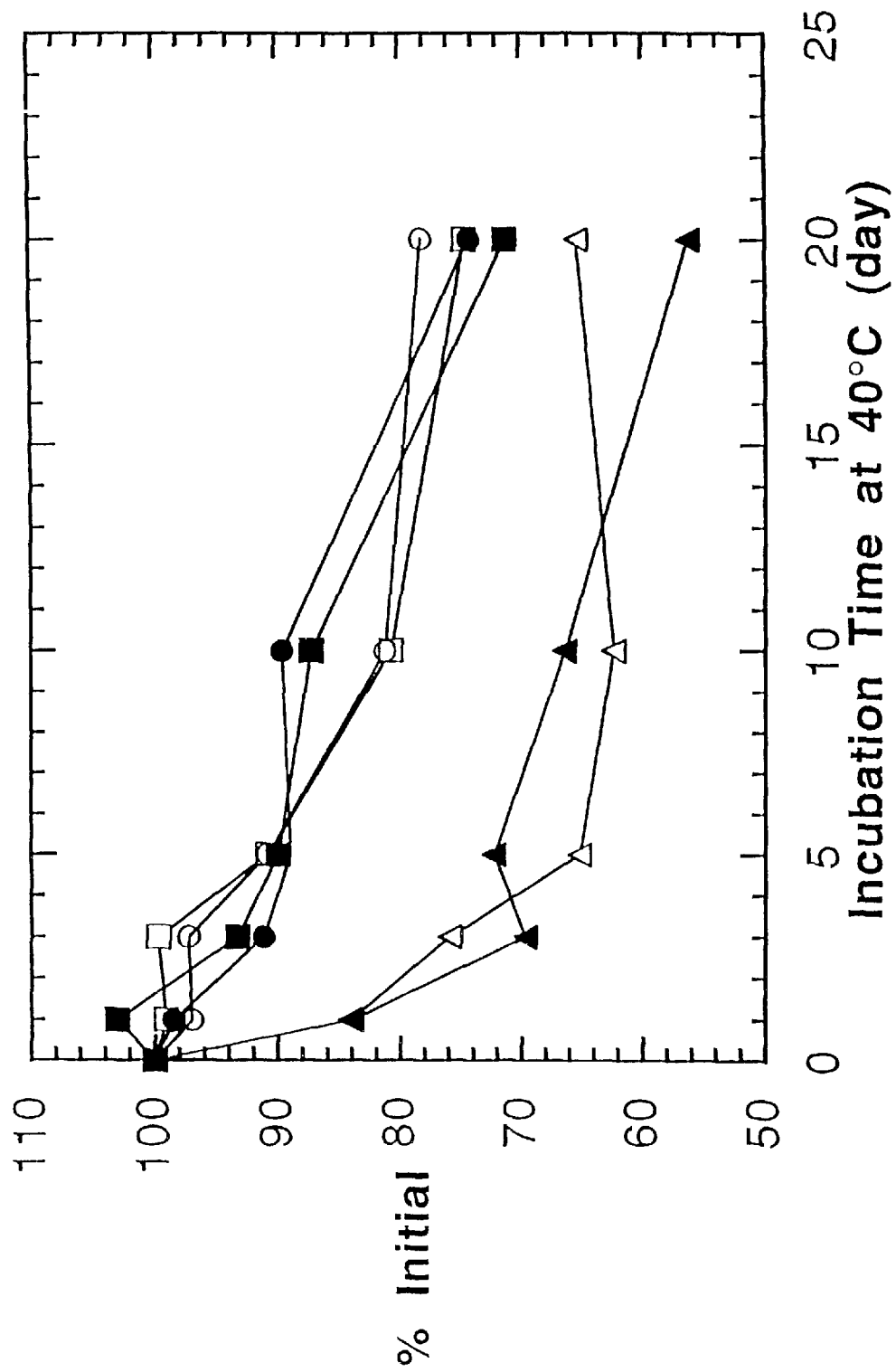
FIG. 8 shows loss of soluble TFPI at 40° C. measured by both cation-exchange HPLC (open symbol) and prothrombin time assay (closed symbol) for 0.5 mg/mL TFPI formulated in 10 mM Na acetate and pH 5.5 containing 150 mM NaCl (triangle) or 8% (w/v) sucrose (square) or 4.5% mannitol (circle).

FIG. 8 shows loss of soluble TFPI at 40° C. measured by both cation-exchange HPLC (open symbol) and prothrombin time assay (closed symbol) for 0.5 mg/mL TFPI formulated in 10 mM Na acetate and pH 5.5 containing 150 mM NaCl (triangle) or 8% (w/v) sucrose (square) or 4.5% (w/v) mannitol (circle).

Figure 9:
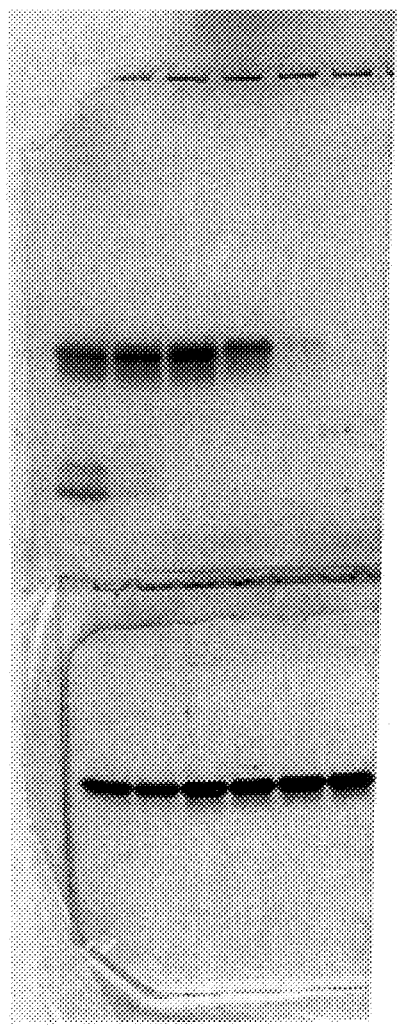
FIG. 9 shows two non-reducing SDS gels for TFPI formulation samples at pH 4 to 9 stored at 40° C. for 0 and 20 days.

FIG. 9 shows two non-reducing SDS gels for TFPI formulation samples in 10 mM NaPO$_4$, 150 mM NaCl, and 0.005% POLYSORBATE-80 at pH 4 to pH 9 stored at 40° C. for 0 days (lower) and 20 days (upper). No loss on TFPI is seen at 0 days. However, at 20 days cleavage fragments of TFPI may be seen at the lower pH range (i.e. pH 4 and pH 5). Without being bound to a particular theory, it is believed that these fragments may result from an acid catalyzed reaction.

Finally, Table 2 shows the half-life of remaining soluble TFPI at 40° C. for various formulations. 0.5 mg/mL TFPI was formulated in these formulation conditions and incubated at 40° C. Samples were withdrawn at predetermined time intervals and loss of soluble and active TFPI were examined by the IEX-HPLC and the PT assay. Half-life for remaining soluble TFPI was then calculated by performing a single exponential fitting to the IEX-HPLC and PT assay results.

TABLE 2

| | t1/2 (day) at 40° C. | |
|---|---|---|
| 0.5 mg/ml TFPI formulated in: | IEX-HPLC | PT assay |
| 10 mM Na Acetate, 150 mM NaCl, pH 5.5 | 10.8 | 17.2 |
| 10 mM Na Citrate, 150 mM NaCl, pH 5.5 | 12.2 | 24.4 |
| 10 mM Na Acetate, 8% (w/v) Sucrose, pH 5.5 | 43.2 | 42.2 |
| 10 mM Na Acetate, 4.5% Mannitol, pH 5.5 | 47.7 | 46.6 |
| 10 mM Na Succinate, 150 mM NaCl, pH 6.0 | 7.8 | 11.0 |
| 10 mM Na Citrate, 150 mM NaCl, pH 6.0 | 13.0 | 18.8 |

TABLE 2-continued

| 0.5 mg/ml TFPI formulated in: | t1/2 (day) at 40° C. | |
|---|---|---|
| | IEX-HPLC | PT assay |
| 10 mM Na Phosphate, 150 mM NaCl, pH 6.0 | 7.8 | 11.2 |
| 10 mM Na Phosphate, 500mM NaCl, pH 6.0 | 52.2 | 68.9 |
| 10 mM Na Citrate, 150 mM NaCl, pH 6.5 | 10.0 | 14.8 |

We claim:

1. A pharmaceutically acceptable composition comprising more than 0.2 mg/mL Tissue Factor Pathway Inhibitor (TFPI) and a solubilizing agent, said solubilizing agent selected from the group consisting of:
   (a) greater than 150 mM sodium chloride;
   (b) isocitrate ion;
   (c) glutamate;
   (d) succinate ion;
   (e) imidazole; and
   (f) SDS, wherein the composition is hypertonic.

2. The composition of claim 1 wherein TFPI is present at a concentration of at least 1 mg/mL.

3. The composition of claim 1 wherein TFPI is present at a concentration of at least 10 mg/mL.

4. The composition of claim 1 further comprising a secondary solubilizer, said secondary solubilizer selected from the group consisting of
   mannitol and
   sorbitol.

5. The composition of claim 1 further comprising sodium phosphate at a concentration greater than 20 mM.

6. The composition of claim 1 wherein the composition comprises 0.5M $Na_3PO_4$.

7. The composition of claim 1 wherein the pH of the composition is below pH 7.0.

8. The composition of claim 7 wherein the pH of the composition is pH 4.5 or below.

9. The composition of claim 1 wherein the solubilizer is acetate ion and the acetate ion is present in the composition as sodium acetate or potassium acetate at a concentration from 5 mM to 20 mM.

10. A pharmaceutically acceptable composition wherein the composition is hypertonic and comprises more than 0.2 mg/ml TFPI and 0.5M NaCl.

11. A pharmaceutically acceptable composition wherein the composition is hypertonic and comprises 0.5M sodium citrate and more than 0.2 mg/ml TFPI.

12. A pharmaceutically acceptable composition comprising more than 0.2 mg/ml TFPI and at least 0.5M sodium chloride.

13. A pharmaceutically acceptable composition comprising more than 0.2 mg/ml TFPI and citrate ion wherein the citrate ion is present in the composition as sodium citrate or potassium citrate at a concentration of from 100 mM to 500 mM.

14. A pharmaceutically acceptable composition comprising more than 0.2 mg/ml TFPI and sodium dodecylsulfate wherein the sodium dodecyl sulfate is present in the composition at a concentration of 0.001% to 0.1% (weight/volume).

* * * * *